United States Patent
Yang et al.

(10) Patent No.: US 7,071,372 B2
(45) Date of Patent: Jul. 4, 2006

(54) METHOD FOR CLONING ANIMALS WITH TARGETTED GENETIC ALTERATIONS BY TRANSFER OF LONG-TERM CULTURED MALE OR FEMALE SOMATIC CELL NUCLEI, COMPRISING ARTIFICIALLY-INDUCED GENETIC ALTERATIONS, TO ENUCLEATED RECIPIENT CELLS

(75) Inventors: Xiangzhong Yang, Storrs, CT (US); Chikara Kubota, Kagoshima (JP)

(73) Assignees: University of Connecticut, Farmington, CT (US); The Governor of Kagoshima Prefecture (JP)

( * ) Notice: Subject to any disclaimer, the term of this patent is extended or adjusted under 35 U.S.C. 154(b) by 441 days.

(21) Appl. No.: 09/755,204

(22) Filed: Jan. 4, 2001

(65) Prior Publication Data

US 2001/0037513 A1 Nov. 1, 2001

Related U.S. Application Data

(60) Provisional application No. 60/174,383, filed on Jan. 4, 2000, provisional application No. 60/174,424, filed on Jan. 4, 2000.

(51) Int. Cl.
*C12N 15/00* (2006.01)
*C12N 15/02* (2006.01)

(52) U.S. Cl. .................. 800/21; 800/24; 800/25; 435/449

(58) Field of Classification Search .......... 435/325, 435/375, 376, 377; 800/24, 8, 13
See application file for complete search history.

(56) References Cited

U.S. PATENT DOCUMENTS

| | | | |
|---|---|---|---|
| 5,888,498 A | 3/1999 | Davis et al. | 424/93.21 |
| 5,945,577 A | 8/1999 | Stice et al. | 800/24 |
| 6,011,197 A | 1/2000 | Strelchenko et al. | 800/24 |
| 6,146,831 A | 11/2000 | Davis et al. | 455/6 |
| 6,235,969 B1 | 5/2001 | Stice et al. | 800/24 |
| 6,235,970 B1 | 5/2001 | Stice et al. | 800/24 |
| 6,258,998 B1 | 7/2001 | Damiani et al. | 800/24 |

FOREIGN PATENT DOCUMENTS

| WO | 07/07669 | 3/1997 |
|---|---|---|
| WO | 97/07668 | 3/1997 |

OTHER PUBLICATIONS

Arbones et al.; Gene targeting in normal somatic cells: inactivation of the interferon-v receptor in myoblasts; Nature Genetics, vol. 6, Jan. 1994; pp 90-97.*

Plump et al; Severe Hypercholesterolemia and Atherosclerosis in Apolipoprotein E-Deficient Mice Created by Homologous Recombination in ES Cells; Cell; vol. 71, 343-353, Oct. 16, 1992.*

Fehilly et al.; Interspecific Chimaerism between sheep and goat; Nature vol. 307, Feb. 16, 1984; pp 634-636.*

Vignon, X. et al, Developmental Potential of Bovine Embryos Reconstructed from Enucleated Mature Oocytes Fused with Cultured Somatic Cells, Comptes Rendus de l'Academie des Sciences/Sciences de la Vie, vol. 321, 1998, pp. 735-745.

Lanza, R.P. et al, Extension of Cell Life-Span and Telomere Length in Animals Cloned from Senescent Somatic Cells, Science, vol. 288, Apr. 28, 2000, pp. 665-669.

Jose B. Cibelli, et al., Cloned Transgenic Calves Produced from Nonquiescent Fetal Fibroblasts, Science, vol. 280, May 22, 1998, pp. 1256-1258.

Angelika E. Schnieke, et al., Human Factor IX Transgenic Sheep Produced by Transfer of Nuclei from Transfected Fetal Fibroblasts, Science, vol. 278, Dec. 19, 1997, pp. 2130-2133.

I. Wilmut, et al., Viable Offspring Derived From Fetal and Adult Mammalian Cells, Nature, vol., 385, Feb. 27, 1997, pp. 810-813.

Yoko Kato, et al., Eight Calves Cloned From Somatic Cells of a Single Adult, Science, vol. 282, Dec. 11, 1998, pp. 2095-2098.

X. Vignon, et al., Development Potential of Bovine Embryos Reconstructed With Somatic Nuclei From Cultured Skin and Muscle Fetal Cells, Theriogenology, p. 392.

D.N. Wells, et al., Production of Cloned Bovine Fetuses Following Nuclear Transfer Using Cells From A Fetal Fibroblast Cell Line, Theriogenology, p. 330.

V. Zakhartchenko, et al., Effects of Serum Starvation and Re-cloning on the Efficiency of Nuclear Transfer Using Bovine Fetal Fibroblasts, Journal of Reproduction and Fertility (1999), vol. 115, pp. 325-331.

Chikara Kubota, et al., Six Cloned Calves Produced From Adult Fibroblast Cells After Long-term Culture, PNAS Feb. 1, 2000, vol. 97, No. 3, pp. 990-995.

K. Shiga, et al., Production of Calves By Transfer of Nuclei From Cultured Somatic Cells Obtained From Japanese Black Bulls, Theriogenology, 1999, vol. 52, pp. 527-535.

Alexander Baguisi, et al., Production of Goats By Somatic Cell Nuclear Transfer, Nature Biotechnology, vol. 17, May 1999, pp. 456-461.

(Continued)

*Primary Examiner*—Joseph Woitach
(74) *Attorney, Agent, or Firm*—Edwards Angell Palmer & Dodge LLP (57) ABSTRACT

An improved method of nuclear transfer employing long-term cultured somatic cells as the donor cells and enucleated oocytes as the recipient cells to produce dividing cybrids. Such cybrids are useful for developing viable animals clones when nurtured in a suitable host environment.

13 Claims, 4 Drawing Sheets

OTHER PUBLICATIONS

T. Wakayama, et al., Full-term Development of Mice From Enucleated Oocytes Injected With Cumulus Cell Nuclei, Nature, vol. 394, Jul. 23, 1998, pp. 369-374.

Keith H.S. Campbell, Nuclear Equivalence, Nuclear Transfer, and the Cell Cycle, Cloning, vol. 1, No. 1, 1999, pp. 3-15.

Philippe Collas, et al., Factors Affecting the Efficiency of Nuclear Transplantation in the Rabbit Embryo, Biology of Reproduction, 1990, vol. 43, pp. 877-884.

Karl Swann, et al., A Novel Signalling Mechanism For Generating $Ca^{2+}$ Oscillations at Fertilization in Mammals, BioEssays, 1997, vol. 19, No. 5, pp. 371-378.

Kenneth L. White, et al., Intracellular Receptors and Agents That Induce Activation in Bovine Oocytes, Theriogenology, 1996, vol. 45, pp. 91-100.

Jean Pierre Ozil, The Parthenogenetic Development of Rabbit Oocytes After Repetitive Pulsatile Electrical Stimulation, Development, 1990, vol. 109, pp. 117-127.

J.L. Susko-Parrish, et al., Inhibition of Protein Kinases After An Induced Calcium Transient Causes Transition of Bovine Oocytes to Embryonic Cycles Without Meiotic Completion, Developmental Biology, 1994, vol. 166, pp. 729-739.

S.M. Mitalipov, Development of Nuclear Transfer and Parthenogenetic Rabbit Embryos Activated With Inositol 1,4,5-Trisphosphate, S.M. Mitalipov, et al., 1999, vol. 60, pp. 821-827.

Lin Liu, et al., Differential Inactivation of Maturation-Promoting Factor and Mitogen-Activated Protein Kinase Following Parthenogenetic Activation of Bovine Oocytes, Biology of Reproduction, 1998, vol. 59, pp. 537-545.

X. Yang, et al., Potential of Hypertonic Medium Treatment For Embryo Micromanipulation: I. Survival of Rabbit Embryos In Vitro and In Vivo Following Sucrose Treatment, 1990, vol. 27, pp. 110-117.

Werner W. Franke, et al., Different Intermediate-Sized Filaments Distinguished By Immunofluorescence Microscopy, Oct. 1978, vol. 75, No. 10, pp. 5034-5038.

Werner W. Franke, et al., Widespread Occurrence of Intermediate-Sized Filaments of the Vimentin-Type in Cultured Cells From Diverse Vertebrates, Experimental Cell Research 123, 1979, pp. 25-46.

Andrew C. Boquest, et al., Flow Cytometric Cell Cycle Analysis of Cultured Porcine Fetal Fibroblast Cells, Biology of Reproduction, 1999, vol. 60, pp. 1013-1019.

R.S. Prather, et al., Cell Cycle Analysis of Cultured Porcine Mammary Cells, Cloning, 1999, vol. 1, No. 1, pp. 17-24.

Jean-Paul Renard, et al., Lymphoid Hypoplasia and Somatic Cloning, The Lancet, May 1, 1999, vol. 353, pp. 1489-1491.

X. Vignon, et al., Development of Bovine Nuclear Transfer Embryos Reconstituted With Quiescent and Proliferative Skin Fibroblasts, Theriogenology, p. 216.

Teruhiko Wakayama, et al., Cloning of Male Mice From Adult Tail-Tip Cells, Nature Genetics, Jun. 1999, vol. 22, pp. 127-128.

David N. Wells, et al., Production of Cloned Calves Following Nuclear Transfer With Cultured Adult Mural Granulosa Cells, Biology of Reproduction, 1999, vol. 60, pp. 996-1005.

S.L. Stice, et al., Donor Blastomere Cell Cycle Stage Affects Developmental Competence of Bovine Nuclear Transfer Embryos, Theriogenology, 1993, vol. 39, p. 318.

Rabindranath de La Fuente, et al., Developmental Consequences of Karyokinesis Without Cytokinesis During the First Mitotic Cell Cycle of Bovine Parthenotes, Biology of Reproduction, 1998, vol. 58, pp. 952-962.

Anneleen Van de Velde, et al., Cell Allocation and Chromosomal Complement of Parthenogenetic and IVF Bovine Embryos, 1999, vol. 54, pp. 57-62.

Xiangzhong Yang, et al., Nuclear Transfer in Cattle: Effect of Nuclear Donor Cells, Cytoplast Age, Co-Culture, and Embryo Transfer, 1993, vol. 35, pp. 29-36.

Giorgio A. Presicce, et al., Nuclear Dynamics of Parthenogenesis of Bovine Oocytes Matured in Vitro for 20 and 40 Hours and Activated With Combined Ethanol and Cycloheximide Treatment, Molec. Reprod. Devel. 1994, vol. 37, pp. 61-68.

Mario R. Capecchi, How Close Are We to Implementing Gene Targeting in Animals Other Than the Mouse?; PNAS, Feb. 1, 2000, vol. 97, No. 3, pp. 956-957.

* cited by examiner

METHOD FOR CLONING ANIMALS WITH TARGETTED GENETIC ALTERATIONS BY TRANSFER OF LONG-TERM CULTURED MALE OR FEMALE SOMATIC CELL NUCLEI, COMPRISING ARTIFICIALLY-INDUCED GENETIC ALTERATIONS, TO ENUCLEATED RECIPIENT CELLS

RELATED ART

This application claims priority from U.S. Provisional Patent Application Nos. 60/174,383 and 60/174,424, filed Jan. 4, 2000, the disclosures of which are incorporated by reference in their entirety herein.

BACKGROUND OF THE INVENTION

1. Field of the Invention

The present invention generally relates to improved methods of nuclear transfer, permitting efficient development of cybrids developed using male, as well as female, donor cells. The present invention provides for the transfer of nuclei of long-term cultured, non-fetal, somatic cells into enucleated oocytes to produce viable totipotent cybrids capable of generating into an embryo, fetus, and/or animal. The present invention further provides for targeted genetic manipulation of the genome of the donor cell to produce a desired genetically-altered animal.

2. Background of the Invention

Recent discoveries in animal cloning have led to a new revolution in science. There is no longer any doubt of the potential applications of cloning technologies in agriculture, medicine and basic biological research. Cloning offers an inexpensive and more effective way to produce transgenic animals than conventional microinjection procedures.

Methods for cloning animals, in particular mammals, have been sought and developed in earnest over the past two decades. A predominant technique used today for cloning is known as "nuclear transfer" or "nuclear transplantation". Nuclear transfer procedures are well known in the art and are described in many references (See, e.g., Campbell et al., *Theriogenology*, 43: 181 (1995); Collas et al., *Mol. Report Dev.*, 38: 264–267 (1994); Keefer et al., *Biol. Reprod.*, 50: 935–939 (1994); Sims et al., *Proc. Natl. Acad. Sci., USA*, 90: 6143–6147 (1993); WO 97/07668; WO 97/07669; WO 94/26884; WO 94/24274; as well as U.S. Pat. Nos. 4,944,384 and 5,057,420 (which describe bovine nuclear transplantation), all of which are incorporated by reference in their entirety herein.

Nuclear transfer protocols typically include the steps of: (1) enucleating an oocyte; (2) isolating a cell to be combined with the enucleated oocyte; (3) inserting the cell, or nucleus isolated from the cell, into the enucleated oocyte to form a cybrid cell; (4) implanting the cybrid into the womb of the animal to form an embryo; and (5) allowing the embryo to develop.

Oocytes are typically isolated from either oviducts and/or ovaries of live animals, although they may be retrieved from deceased animals as well. Oocytes are typically matured in a variety of medium known to those of ordinary skill in the art prior to enucleation. Generally the oocytes used in nuclear transfer techniques are in the metaphase II cell-cycle stage. It is generally believed that oocytes are best fresh and non-preserved. Certain oocytes, such as cattle oocytes, are extremely sensitive to low temperatures and have not been found to be very useful after cryopreservation.

Enucleation of the oocyte can be performed in a number of manners, well known to those of ordinary skill in the art, including, aspiration (Smith & Wilmut, *Biol. Reprod.*, 40: 1027–1035 (1989)), by use of DNA-specific fluorochromes (See, e.g., Tusnoda et al., *J. Reprod. Fertil.* 82: 173 (1988)), and irradiation with ultraviolet light (See, e.g., Gurdon, Q. J. *Microsc. Soc.*, 101: 299–311 (1960)). Enucleation may also be effected by other methods known in the art, such as described in U.S. Pat. No. 4,994,384, herein incorporated by reference. Preferably, the oocyte is exposed to a medium containing a microfilament disrupting agent or tubulin-disrupting agent prior to and during, enucleation. Disruption of the microfilaments imparts relative fluidity to the cell membrane and underlying cortical cytoplasm such that a portion of the oocyte enclosed within the membrane can easily be aspirated into a pipette with minimal damage to cellular structures.

Until recently, donor nuclei have been conventionally isolated almost entirely from primordial germ cells and somatic embryo cells. During development certain genes are known to be altered in such a manner that they are no longer transcribed, so-called "imprinted". Studies on imprinting have shown that "imprinting" is removed during germ cell formation (i.e. reprogramming).

It was not until the mid-1990's that reports of nuclear transfer form cultured cell lines arose. These reports (See, e.g., Wilmut et al., *Nature (London)* 385, 810–183) (1997)) suggest the usefulness of donor cells derived not only from embryos, but also, blastocysts, ovaries and other reproductive and sexually-related cells/tissues (e.g. the mammary epithelial cells, cumulus cells). Prior to the present invention, somatic cells derived from non-embryonic and non-reproductive/sexually related tissues (hereinafter referred to as, "NENS somatic cells") were not found to be useful as donor cells in producing viable animal clones. In fact, as stated in U.S. Pat. No. 5,945,577 to Stice et al., until the late 1990s it was widely believed that only embryonic or undifferentiated cell types could direct any sort of fetal development in nuclear transfer techniques.

U.S. Pat. No. 5,945,577 to Stice et al., teaches advanced embryonic and fetal development from nuclear transfers from differentiated donor somatic cells to enucleated oocytes. U.S. Pat. No. 6,022,197 to Strelchenko et al., states that fibroblasts from a fibroblast cell culture derived from an adult ear punch may be used as nuclear donors in a nuclear transfer process. Both references, however, fail to demonstrate any viable animals being produced by their methodologies with NENS somatic cell nuclei donation.

With regard to somatic donor cells, prior to the present invention successful cloning experiments (that is, producing viable animal clones) have all entailed using donor nuclei from female donors. Researchers generally entertained the possibility that only female somatic cells associated with a reproductive organ(s) retain the capacity to be properly re-programmed by an oocyte environment (See, e.g., Capecchi, *PNAS* 97: 956–957 (Feb. 1, 2000)). That is, it was believed that male cells did not permit the proper execution of the complex changes in the patterns of genomic demethylation and methylation that normally accompany the process of early embryogenesis (which is necessary to maintain balanced growth between extra-embryonic and fetal tissues—See, e.g., Tilghman, S. M. *Cell* 96: 185–193 (1999)) due to an inherent incompatibility between male somatic nuclei and female oocyte cytoplasm (See, e.g., Capecchi, *PNAS* 97: 956–957 (Feb. 1, 2000)).

The miotic cell cycle is generally divided into four distinct phases: G1, S, G2, and M. The so-called "start event", that is, the commitment to undergo another cell cycle, is made in the G1 phase. Once the "start event" has occurred, a cell passes through the remainder of the G1 phase which is a pre-DNA synthesis stage. The S phase which follows is when DNA synthesis takes place. The G2 phase is the period between DNA synthesis and mitosis. Mitosis occurs at the M phase. The donor nucleus (preferably in the G0 or G1 phase) is conventionally introduced into the recipient cells in the M phase of the cell cycle by either fusion or direct injection.

The donor cell is typically transferred into the perivitelline space of a enucleated oocyte to produce the cybrid. The recipient oocytes are conventionally arrested in the metaphase of the second meiotic division prior to fusion with the donor cell.

Fusion is typically induced by application of a DC electrical pulse across the contact/fusion plane, but additional AC current may be used to assist alignment of donor and recipient cells. Electrofusion produces a pulse of electricity that is sufficient to cause a transient breakdown of the plasma membrane and which is short enough that the membrane reforms rapidly. Fusion may also be induced by exposure of the cells to fusion-promoting chemicals, such as polyethylene glycol, or by way of an inactivated virus, such as the Sendai virus. In the case of small donor nuclei, microinjection directly into the oocyte may be preferred over fusion.

A cybrid is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated cybrids, or embryos, are typically cultured in medium well known to those of ordinary skill in the art, and include, without limitation, Tissue Culture Medium-199 (TCM-199)+10% fetal calf serum, Tyrodes-Albumin-Lactate-Pyruvate (TALP), Ham's F-10+10% fetal calf serum (FCS), synthetic oviductal fluid ("SOF"), $B_2$, $CR_{1aa}$, medium and high potassium simplex medium ("KSOM").

The construction of embryos by nuclear transfer was first proposed by Spemann in the 1930s (Spemann, *Embryonic Development and Induction* 210–211, Hofner Publishing Co., New York (1938). It wasn't, however, until the early 1950s that it was demonstrated that nuclei could direct development (Briggs and King, *Proc. Natl. Acad. Sci. USA* 38 455–461 (1952)). The first successful nuclear transfer experiment using mammalian cells was reported by McGrath & Solter in 1983, wherein isolated pronuclei from a murine (mouse) zygote were inserted into an enucleated oocyte to result in live offspring (McGrath & Solter, *Science* 220: 1300–1312 (1983)).

One of first nuclear transfer experiments utilizing ovine embryonic cells as nuclear donors was reported by Willadsen in 1986 (Willadsen, *Nature* 320: 63–65 (1986)). Reports of cloning of animals using ovine embryonic cells as the nuclear donor occurred in the mid-1990s (Campbell et al., *Nature* 380: 64–66 (1996)); PCT Publication WO 95/20042). It was not, however, arguably not until 1997 that cloning of ovine animals became practicable using a technique described by Wilmut et al., (Wilmut et al., *Nature* 385: 810–183 (1997)). The Wilmut et al., publication describes a procedure which entails methodology for making the donor cell quiescent prior to the nuclear transfer. Ovine animals were produced using a mammary semantic cell donor and an enucleated oocyte.

The cloning of bovine animals using nuclear transfer techniques has not been reported to be as successful as in murine and ovine animals. Most reports have reported embryos that do not survive post utero. However, there are isolated reports of the successful cloning of cows (See, Kato et al., *Science* 282: 2095–2098 (1998); Wells et al., *Biol. Reprod.* 60: 996–1005 (1999); and Strelchenko et al., U.S. Pat. No. 6,011,197 (Issue Date: Jan. 4, 2000).

A major problem with all presently available nuclear transfer techniques is that they typically require donor cells which are relatively difficult to harvest and maintain, they require the use of relatively fresh donor cells or briefly cultured donor cells, cloning efficiency is low and they do not permit directed employment of genome manipulation techniques.

A large number of nuclear transfer studies have made use of embryonic cells or ovary cells as donor cells. The embryonic stem cell has been found to be a particularly useful cell as a donor cell in that it supports the development of enucleated oocytes to term. Genetic manipulation of mouse embryonic stem cells has revolutionized mouse genetic research. Unfortunately, embryonic stem cells are not readily available in other species.

The use of ungulate inner cell mass cells for nuclear transplantation has also been reported. Isolation of such cells tends to be cumbersome in particular given the need of these techniques for relatively fresh donor cells (which are available in low numbers) in order to make the cybrid. For example, embryonic cell lines used in a number of prior art nuclear transfer clonings were derived from embryos of less than 10 days gestation and were stored less than about 5 passages (See, e.g., Campbell et al., *Nature*, 380: 64–68 (1996); Stice et al., *Biol. Reprod.*, 54: 100–110 (1996)). Such cells are also typically maintained on a feeder layer to prevent overt differentiation of the donor cell to be used in the cloning procedure. Because of the problems associated with harvesting such cells, a number of researchers have proposed using somatic cells as donor cells.

The major problem associated with somatic cell nuclear transfer has been a very low cloning efficiency. The efficiency of live births from somatic cell cloning using the method of cloning described by Wilmut et al., (Wilmut et al., *Nature* 385: 810–183 (1997)) has been estimated to be approximately 1 out of 300, that is, the cloning efficiency is at best 0.4% (i.e. number of cloned lambs divided by the number of nuclear transfers used to produce that number of cloned lambs). It is clear that the low cloning efficiency has significantly reduced commercialization prospects for such technology.

Successful somatic cell cloning has been largely limited to the use of donor cells that are either fresh (Wakayama et al., *Nature (London)* 394: 369–374 (1998)) or after short-term (under 10 passages) in vitro culture (Wilmut et al., *Nature (London)* 385: 810–813 (1997); Kato et al., *Science* 282: 2095–2098 (1998); Wells et al., *Biol. Reprod.* 60: 996–1005 (1997)); Schnieke et al., *Science* 278: 2130–2133 (1997); Cibelli et al., *Science* 280: 1256–1258 (1998)), which do not permit targeted gene manipulations, given the limitations of present technology.

There is a need, therefore, for a somatic cell nuclear transfer cloning technique which provides for the use of long-term cultured donor cells which retain the ability to produce cybrids capable of developing into viable animals, that provides for high cloning efficiency with easily harvested somatic donor cells, and that provides the opportunity to employ genetic manipulation techniques, in particular gene knock-out techniques, prior to formation of the cybrid.

DEFINED TERMS

Activation: By the term "activation" it is meant to refer to any materials and methods useful for stimulating a cell to divide before, during, and after a nuclear transfer step.

Animal Clone: By the term "animal clone" it is meant a viable animal having a genome that is substantially similar or identical to the genome of another animal and which is produced by other than fusion of a sperm and nucleated oocyte. By "substantially similar" it is meant that the genes differ by copy error differences that normally occur during the replication of DNA.

Clone: By "clone" it is meant a biomass having a nuclear DNA sequence that is substantially similar to or identical, to the nuclear DNA sequence of another biomass (such as a cell, an organ, fetus, animals etc.). By "substantially similar" it is meant that the two sequences may differ by copy error differences that normally occur during the replication of a nuclear DNA.

Cloning Efficiency: By "cloning efficiency" it is meant the efficiency of production of an animal clone from a cybrid.

Cumulus Cell: By "cumulus cell" it is meant any cultured or non-cultured cell isolated from cells and/or tissue surrounding an oocyte.

Cybrid: By "cybrid" it is meant a construction wherein an entire nuclear donor is translocated into the cytoplasm of a recipient cell such as an oocyte.

Embryo: By the term "embryo" it is meant a developing cell mass that has not implanted into the uterus of maternal host. By the term "embryo" it is meant to include a fertilized oocyte, a cybrid, a pre-implantation stage developing cell mass, etc.

Fetus: By the term "fetus" it is meant a developing cell mass that has implanted into the uterus of material host.

Fibroblast: By "fibroblast" it is meant a cell-type present in vertebrate connective tissue that secretes tropocollagen and mucopolysaccharides which constitute the connective tissue ground substance. Fibroblast cells normally stain positive for vimentin and negative for cytokeratin stains.

Fibroblast-like Cell: By "fibroblast-like cell" it is meant cultured cells that have a distinct flattened morphology and are capable of growing within monolayers in culture.

Fusion: By "fusion" it is meant the combination of portions of lipid membranes corresponding to the cell nuclear donor and the recipient oocyte.

Genetically-Altered Animal: By "genetically-altered animal" it is meant an animal carrying a gene mutation introduced by genetic engineering techniques Genetically-Altered Cell: By "genetically-altered cell" it is meant a cell carrying a gene mutation introduced by genetic engineering techniques Inner Cell Mass: By "inner cell mass" it is meant the cells that give rise to the embryo proper.

Long-Term Culture: By the term "long-term culture" it is meant cells that have been cultured for 10 or more passages in a suitable growth medium.

Modified Nuclear DNA: By "modified nuclear DNA" it is meant nuclear deoxyribonucleic acid that has been manipulated by one or more recombinant DNA techniques.

NENS Somatic Cell: By the term "NENS Somatic Cell" it is meant a somatic cell that is derived from a source other than from an embryo, blastocyst, fetus or sexually-related tissue, such as the ovaries, oviducts, mammary glands, reproductive tract etc.

Nuclear Transfer: By the term "nuclear transfer" it is meant introducing a full complement of nuclear DNA from one cell into an enucleated cell.

Pluripotent: By the term "pluripotent" it is meant to refer to the capacity of a cell to differentiate into a sub-population of cells within a developing cell mass but not to give rise to all of the cells in such cell mass, such as an embryo, fetus or animal.

Quiescent Cell: By "quiescent cell" it is meant a cell that is not dividing.

Reprogramming: By "reprogramming" it is meant the materials and methods that can convert a non-totipotent cell into a totipotent cell.

Serum Starve: By "serum starve" it is meant culturing cells in a medium comprising a serum concentration sufficiently low to render cultured cells quiescent.

Somatic Cell: By the term "somatic cell" it is meant to refer to a cell other than a germ cells.

Term Animal: By the term "term animal" it is meant an animal capable of surviving one or more weeks outside of the environment where it developed (e.g., uterus) without the need for life support or medical intervention. By "full term animal" it is meant a term animal which is physiologically developed within the norms for neonates of such animals.

Totipotent: By the term "totipotent" it is meant the capacity of a cell to give rise to all of the cells in a developing cell mass, such as an embryo, fetus or animal (as opposed to a "pluripotent" cell).

Transgenic Animal: By the term "transgenic animal" it is meant an animal with a genome produce in whole or in part by artificial genetic manipulation means.

Ungulate: By the term "ungulate" it is meant to refer to a four-legged animal having hooves.

Viable Animal: By the term "viable animal" it is meant an animal capable of surviving for more than 365 days outside of a host animal without the need for artificial life support or medical intervention.

SUMMARY OF THE INVENTION

The present invention provides improved nuclear transfer cloning in that it increases embryo development to blastocyst stage, cybrid impregnation rates, and birth rate. Such effects are effectuated by using nuclear donor cells kept in long-term culture for more than five, preferably more than seven, more preferably more than ten, and yet more preferably more than 15 passages. The present invention further provides a method for maintaining the totipotency, and cloning competency, of nuclear donor cells during prolonged culture. Such method provides nuclear donor cells which offer cloning competence after ten or more passages which is equivalent to, or better than, that provided by freshly harvested nuclear donor cells. Such method permits for the first time targeted gene manipulations of somatic nuclear donor cells prior to nuclear transfer by permitting gene manipulation techniques known in the art to be employed during the in vitro culture. As would be understood by one of ordinary skill in the art, cloning using site-specific genetically manipulated cells is a valuable tool with applications in agriculture, medicine, and basic biological research.

In one embodiment of the present invention, there is provided an improved method of cloning a viable animal by nuclear transfer comprising the steps of: (a) inserting a somatic cell, or nucleus isolated from said somatic cell, deriving from a somatic cell culture having undergone 5 or more passages, into an enucleate oocyte to form a cybrid; (b) activating the cybrid; (c) culturing the activated cybrid; (d) transferring the activated cybrid of step (c) into an appropriate host such that the activated cybrid develops into a fetus; (e) maintaining the fetus in the host until the fetus is capable of surviving and maturating into a viable animal outside of said host. The cybrid, activated cybrid, fetus and animal produced during the steps of such method, and cells, nuclei, and other cellular components which may be harvested therefrom, are also asserted as embodiments of the present invention.

In another embodiment of the present invention there is provided an improved method of cloning a mammal by nuclear transfer comprising the introduction of a donor cell from the mammal, or donor cell nucleus, into an enucleated oocyte of the same species as the donor cell to form a cybrid, inserting the cybrid into the uterus of a host mother of said species so as to cause implantation of the cybrid into the uterus to form a fetus, and permitting the fetus to develop into the cloned mammal wherein the improvement comprises using as the donor cell, or donor cell nucleus, a somatic cell that has been cultured for more than five (5) passages.

And yet further provided is a method for cloning an animal, more particularly a mammal, and yet more particularly a ungulate, said method comprising the steps of: (a) obtaining NENS somatic cells; (b) culturing said NENS somatic cells for 5 or more passages; (c) inserting the cultured NENS somatic cells of step (b), or nucleus isolated from said cultured NENS somatic cell, into an enucleate oocyte to form a cybrid; (d) activating the cybrid; (e) culturing the activated cybrid; (f) transferring the activated cybrid of step (e) into an appropriate host such that the activated cybrid develops into a fetus; (g) maintaining the fetus in the host until said fetus is capable of surviving and maturating into a viable animal outside of said host. The cybrid, activated cybrid, fetus and animal produced during the steps of such method, and cells, nuclei, and other cellular components which may be harvested therefrom, are also asserted as embodiments of the present invention.

A preferred donor cell of the present invention is a somatic cell, more particularly a NENS somatic cell. A particularly preferred donor cell is a NENS fibroblast-like cell, more preferably a NENS fibroblast. Cloning using fibroblasts, such as skin cells, offers the advantage of easy accessibility and non-invasiveness without animal sex or age limitations.

Prior to the present invention, the overall cloning efficiency using somatic cells of all types has been low, ranging from 0 to nearly 10%. No report of repeatable successful cloning of viable animals using nuclear transfer from donor NENS somatic cells to recipient cells had been reported The present invention permits cloning efficiencies of greater than 10%, in the range of 15% or more. Significantly higher pregnancy rates and birth rates are noted as compared to prior somatic cell nuclear transfer clonings.

Therefore, there is provided by the present invention a method for cloning an animal, particularly a mammal, with a cloning efficiency of better than ten percent (10%), said method comprising the steps of: (a) inserting a somatic cell, or nucleus isolated from said somatic cell, deriving from a somatic cell culture having undergone 5 or more passages, into an enucleate oocyte to form a cybrid; (b) activating the cybrid; (c) culturing the activated cybrid; (d) transferring the activated cybrid of step (c) into an appropriate host such that the activated cybrid develops into a fetus; (e) maintaining the fetus in the host until the fetus is capable of surviving and maturating into a viable animal outside of said host. The cybrid, activated cybrid, fetus and animal produced during the steps of such method, and cells, nuclei, and other cellular components which may be harvested therefrom, are also asserted as embodiments of the present invention.

In a preferred embodiment of the present invention, somatic cells are cultured for 5 or more passages (about 10 doublings in cell number), more preferably for 7 or more passages (about 14 doublings in cell number), more preferably for 10 (about 20 doublings in cell number) or more passages and yet more preferably for 15 (about 30 doublings in cell number ) passages on a suitable growth medium. Advantageously cells are cultured until confluent, disaggregated by chemical and/or mechanical means, and allocated to new growth media upon each passage.

It is preferred that the donor cells of the present invention be induced to quiescence prior to fusion or microinjection into the recipient cell. In accord with the teachings of PCT/GB96/02099 and WO 97/07668, both assigned to the Roslin Institute (Edinburgh), it is preferred that the donor nucleus be in either the G0 or G1 phase of the cell cycle at the time of transfer. Donors must be diploid at the time of transfer in order to maintain correct ploidy of the cybrid. It is particularly preferred that the donor cells be in the G0 phase of the cell cycle.

The present invention provides a manner for cloning a male animal, preferably a male mammal, using nuclear transfer techniques. It is believed that the present inventors are the first to have successfully cloned a viable male animal (in particular a viable male mammal) using nuclei derived from a male donor (See, Capecchi et al., *PNAS* 97: 956–957, at page 957 (Feb. 1, 2000)). While U.S. Pat. No. 6,011,197) suggests that a single male Holstein was produced using embryonic germ cells as the donor cells, it is unknown whether such animal was a "viable animal" as defined herein. Further, such animal was produced using germ cells derived from an embryo, and a double nuclear transfer procedure, which significantly reduces the commercial usefulness of such approach.

The present inventors note statements in U.S. Pat. No. 6,011,197 to the effect that "virtually any type of precursor cell" can be used to form its "immortalized, totipotent" donor cells (col. 30, lines 24–25 of U.S. Pat. No. 6,011,197 (e.g., cells reprogrammed by culture with LIF (leukemia inhibitor factor) and FGF (fibroblast growth factor)), that such cells can be used in a nuclear transfer process to generate a cloned embryo (col. 37, lines 19–20 of U.S. Pat. No. 6,011,197), that generated embryos can be implanted in uterus or artificial uterine environment (col. 41, lines 59–60 of U.S. Pat. No. 6,011,197), and that such embryo can develop to term (col. 42, line 17 of U.S. Pat. No. 6,011,197), but note only embryos being produced from embryonic germ cells. Applicants further note U.S. Pat. No. 5,945,577 to Stice et al. which asserts that genetically-altered animals may be produced by insertion of foreign heterologous DNA into embryonic, as well as adult, fibroblast cells with nuclear transfer of the altered DNA into an enucleated oocyte. Applicants note no demonstration in the Stice et al. patent of viable animals. Applicants further note that the only transgenic fetuses reported in the patent were produced using embryonic cells derived from intermediary embryos (i.e, involving double nuclear transplantation). The Applicants further note that the genetic-alterations introduced into the fetal DNA of the fetuses produced by Stice et al. were not targeted-genetic alterations, but were rather, non-specific, random, alterations. Applicants assert that targeted-genetic alterations were not possible without an understanding of the utility of somatic cells derived from long-term somatic cultures in nuclear transfer and the advantageous nature of such long-term culture.

The present invention further provides, therefore, a method for the cloning of male animals, in particular male mammals, using nuclei of somatic cells, preferably fibroblasts or fibroblast-like cells, harvested from male animals. The method comprising the steps of: (a) inserting a male somatic cell, or nucleus isolated from said somatic cell, deriving from a somatic cell culture having undergone 5 or more passages, into an enucleate oocyte to form a cybrid; (b) activating the cybrid; (c) culturing the activated cybrid; (d) transferring the activated cybrid of step (c) into an appropriate host such that the activated cybrid develops into a fetus; (e) maintaining the fetus in the host until the fetus is capable of surviving and maturing into a viable animal outside of said host. The cybrid, activated cybrid, fetus and animal produced during the steps of such method, and cells, nuclei, and other cellular components which may be harvested therefrom, are also asserted as embodiments of the present invention.

While it is preferred that the recipient of the donor cell nucleus be an oocyte at metaphase I to metaphase II, the present invention may be used with other recipients known to those of ordinary skill in the art including zygotes and two-cell embryos. Activation of oocytes may be by fertilization with sperm or by parthenogenetic activation schemes known in the art. It is particularly preferred that the recipient be enucleate. A preferred oocyte is an enucleated metaphase II oocyte, non-activated or pre-activated. When a recipient is an enucleated metaphase II oocyte, activation may take place at the time of transfer.

It is preferred that the cybrid be activated prior to implantation into the host using techniques known to those of ordinary skill in the art, such as electrical stimulation. Non-electrical means for activation known in the art include, ethanol, protein kinase inhibitors (e.g., 6-dimethylpurine (DMAP), ionophores (e.g., ionomycin), temperature change, protein synthesis inhibitors (e.g. cyclohexamide), thapsigargin, phorbol esters (e.g. phorbol 12-myristate 13-acetate ("PMA")), and mechanical means (See, e.g., Susko-Parrish et al., U.S. Pat. No. 5,496,720, issued Mar. 5, 1996).

As would be understood by one of ordinary skill in the art, activation techniques should be optimized for the particular cell line being used. For example, Ozil et al., *Development* 109: 117–127 (1990), report that only a select series of pulses and control of $Ca^{2+}$ was able to promote diploidized rabbit oocytes to mid-gestation. The interval of pulses for electrical activation in a rabbit is reported to be about 4 minutes (Ozil et al., *Development* 109: 117–127 (1990)), while that in a mouse has been reported to be about 10 to 20 min (Cutberson et al., *Nature* 316: 541–542 (1985)), and that in a cow about 20 to 30 minutes (Robl et al., in *Symposium on Cloning Mammals by Nuclear Transplantation* (Seidel ed.), Colorado State University, 24–27 (1992)).

The present inventors have found for a Japanese Black Beef bull that two pulses of direct current of 2.5 kV/cm for 10 μsec using an Electrocell Manipulator 200 (BTX, San Diego) at fusion stage, followed by culturing with cyclohexamide (10 μg/ml; Sigma Chemical) in CR1aa medium for 5 additional hours activated the cybrid so as to not only proceed to the blastocyst stage, but to the development of a fetus capable of surviving to term.

The present inventors have discovered that improved activation of the cybrid to blastocyst stage, but not necessarily to term, can be effectuated by exposing the cybrid or enucleated oocyte (the "cytoplast") first to a protein kinase inhibitor, such as 6-dimethylaminopurine (DMAP), and then to electric pulse stimulation. However, it was found that blastocysts produced by this method may be deficient in the DNA reprogramming of the donated nucleus which is necessary for the blastocyst to develop into a fetus. There is provided, however, by the present invention a method for improving blastocyst development from cybrids produced by nuclear transfer from a donor cell to an enucleated oocyte, said method comprising activating the enucleated oocyte with a protein kinase inhibitor prior to fusion with the donor cell nucleus and electrostimulating the cybrid during or after fusion.

Cultured donor cells may be genetically altered by methods well-known to those of ordinary skill in the art. See, *Molecular Cloning a Laboratory Manual,* 2nd Ed., 1989, Sambrook, Fritsch and Maniatis, Cold Spring Harbor Laboratory Press; U.S. Pat. No. 5,612,205, Kay et al., issued Mar. 18, 1997; U.S. Pat. No. 5,633,067, to DeBoer et al., issued May 27, 1997. Any known method for inserting, deleting or modifying a desired gene from a mammalian cell may be used to alter the nuclear donor. Included is the technique of homologous recombination, which allows the insertion, deletion or modification of a gene or genes at specific site or sites in the cell genome. Examples for modifying a target DNA genome by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In such vein, further provided is a method for producing an animal clone with genetically-engineered targeted genetic alterations, said method comprising the steps of: (a) culturing a somatic cell for five (5) or more passages to produce a long-term culture; (b) altering in a targeted manner the nuclear DNA of somatic cells of the long-term culture of step (a); (c) inserting the altered nuclear DNA of the somatic cells of step (b) into an enucleate oocyte to form a cybrid; (d) activating the cybrid; (e) culturing the activated cybrid to form an embryo; (f) transferring the embryo into an appropriate host such that the embryo develops into a fetus; (g) maintaining said fetus in said host until said fetus is capable of surviving and maturing into a viable animal outside of said host. The cybrid, activated cybrid, embryo, fetus and animal produced during the steps of such method, and cells, nuclei, and other cellular components which may be harvested therefrom, are also asserted as embodiments of the present invention.

In another embodiment of the present invention there is proved an improved method of cloning a mammal by nuclear transfer comprising the introduction of a donor cell from the mammal, or donor cell nucleus, into an enucleated oocyte of the same species as the donor cell to form a cybrid, inserting the cybrid into the uterus of a host mother of said species so as to cause implantation of the cybrid into the uterus to form a fetus, and permitting the fetus to develop into the cloned mammal wherein the improvement comprises using as the donor cell, or donor cell nucleus, a somatic cell that has been cultured for more than five (5) passages, and wherein the donor cell, or donor cell nucleus, has been genetically transformed to comprise at least one addition, substitution or deletion of a nucleic acid or nucleic acid sequence.

The present invention is in principle applicable to all animals, including birds, amphibians and fish species. However, its greatest commercial usefulness presently envisioned is for non-human mammals. Its applicability extends not only to the family of ruminants belonging to the genus Bos (so called "bovines" which include cattle, oxen, sheep, and goats) but to other ungulates such as camels, pigs and water buffalo.

BRIEF DESCRIPTION OF THE DRAWINGS

The file of this patent contains at least one photograph executed in color. Copies of this patent with color drawing(s) will be provided by the Patent and Trademark Office upon request and payment of the necessary fees.

The accompanying drawings, which are incorporated in and constitute part of the specification, illustrate presently preferred embodiments of the invention, and together with the general description given above and the detailed description of the preferred embodiments given below, serve to explain the principles of the invention. They should not be construed as limiting on the invention described herein.

DETAILED DESCRIPTION OF THE INVENTION

The present invention provides for the production of site-specific genetically-modified animals using nuclear transfer techniques. It also provides for the successful and repeatable cloning of viable animals from somatic cells, in particular NENS somatic cells, derived from either a male or female donor.

The present inventors have discovered genetic totipotency of cells after 5 or more passages, more particularly after long-term culture, and yet more particularly after 15 or more passages. Such discovery was made in the face of prevailing wisdom that long-term culture of donor cells, in particular somatic cells, would comprise the capacity of the cells to generate healthy animal clones. Contrary to such prevailing thought, the present inventors have discovered that cloning efficiency is improved upon culture of donor cells, in particular somatic cells (and more particularly NENS fibroblast or NENS fibroblast-like cells) for 5 or more passages, and that unexpectedly more improved cloning efficiencies could be attained when such cells undergo long-term culture. It is not clear how successive culture improves the nuclear totipotency of donor cells.

The present method can in particular be used to produce clones using skin cells as the cell donors. Cloning by using skin cells offers the advantage of easy accessibility and noninvasiveness without animal sex or age limitations. Previously, successful cloning of adult animals has largely been limited to the use of female reproductive system cells: e.g., mammary epithelial cells (Wilmut et al., *Nature (London)* 385: 810–813 (1997)), cumulus cells (Kato et al., *Science* 282: 2095–2098 (1998); Wells et al., *Biol. Reprod.* 60: 996–1005 (1999)), or oviductal epithelial cells (Kato et al., *Science* 282: 2095–2098 (1998)). Although skin cells from a 2-week-old calf were successfully cloned, the single calf produced from that study survived only 7 weeks and died of lymphoid hypoplasia (Renard et al., *Lancet* 353: 1489–1491 (1999)). In mice, tail-tip cells from a 10- to 12-week-old mouse have been used for cloning, and only one viable clone was produced from 274 embryos (Wakayama et al., *Nat. Genet.* 22: 127–128 (1999)). The findings of the present invention, therefore, have important implications for tissue banking and preservation of endangered species.

Genetic manipulation of mouse embryonic stem cells has revolutionized mouse genetic research. However, embryonic stem cells are not available in other species. As prior art successes in cloning have been limited to the use of cells collected either fresh (Wakayama et al., *Nature (London)* 394: 369–374 (1998)) or after short-term (under 10 passages) in vitro culture (Wilmut et al., *Nature (London)* 385: 810–813 (1997); Kato et al., *Science* 282: 2095–2098 (1998); Wells et al., *Biol. Reprod.* 60: 996–1005 (1999); Schnieke et al., *Science* 278: 2130–2133 (1997); Cibelli et al., *Science* 280: 1256–1258 (1998)), targeted gene manipulations have not been producible in any species other than the mouse.

The demonstration by the present inventors of genetic totipotency of cells after prolonged culture is pivotal to combining site-specific genetic manipulations and cloning. The present inventors have shown both that fibroblasts of aged animals remain competent for cloning, and prolonged culture does not affect the cloning competence of adult somatic donor cells.

The long-term culture of donor cells has allowed the present inventors to selectively target gene changes in the genome of the donor cell, or selectively turn-off genes, using gene alteration and "knock-out" methods well known in the art. By gene targeting it is meant not only the inactivation of a gene but also altering of gene activity in any purposeful manner. Nuclei from such genetically-altered donor cells can then be used in nuclear transfer techniques as described herein to ultimately produce viable animals carrying the targeted genetic changes in their genomes. Animals produced using such gene targeting and cloning technique can be used to determine the function of a particular blocked gene, the importance of the conservation of a gene sequence, and as models for disease states, as well as for other purposes readily apparent to one of ordinary skill in the art. For example, the gene(s) responsible for certain immunological recognition proteins might be altered such that tissue from the host animal might be immunologically-acceptable by other animals (such as pig tissue being used in humans), or a gene(s) altered to produce a more commercially acceptable animal (e.g., a cow that produces more milk).

In one aspect of the invention there is provided a process by which genetically-altered and non-genetically altered animals may be produced, such process comprising the steps of: (a) isolating a diploid donor cell; (b) culturing the diploid donor cell for more than 10 doublings, preferably more than about 20 doublings, and yet more preferably more than 30 doublings, on a medium constituted such that the diploid donor cell multiplies; (c) optionally altering, preferably in a targeted manner, the genome of one or more cells of the diploid donor cells of step (b); (d) optionally screening and selecting from the cells of step (c) stable desired mutants; (e) reconstituting an embryo employing the nuclei transfer techniques using nuclei from the cells of step (b), or optionally steps (c) or (d); (f) culturing the embryo in vivo or in vitro to a blastocyst; (g) optionally screening and selecting from the blastocysts of step (f) stable desired mutants; (h) transfer of the blastocyst to medium capable of allowing the blastocyst to develop into a term animal.

A particularly preferred donor cell is the fibroblast or fibroblast-like cell. Fibroblast cells may be collected from an ear skin biopsy. In a method of preparation found advantageous, the tissue biopsy is cut into small pieces (3 mm$^2$) and the pieces as tissue explants are cultured in DMEM (Gibco, 15) plus 10% fetal bovine serum (FBS) and antibiotics (Gibco, cat#15240-013) at 37.5° C. in a humidified atmosphere of 5% $CO_2$ and 95% air. After a week in culture, fibroblast cell monolayers form around the tissue explants. The explants are then removed to start new culture and the fibroblast cells are harvested weekly for freezing. For long term storage, the cultured cells may be collected following trypsin treatment, frozen in 10% dimethyl sulfoxide (Sigma) and stored in liquid nitrogen. Upon use for nuclear transfer, cells are thawed and cultured to confluency for passage. For each passage (estimated 2 cell doublings per passage), cells are cultured until confluent, disaggregated by incubation in a 0.1% (w/v) trypsin (Difco) and EDTA (Nacalai) solution for 1 min at 37° C. and allocated to three new dishes for further passaging. Normally, each passage lasts about 6 days.

Confirmation of fibroblast phenotype of donor cells may be conducted by immunocytochemical staining with monoclonal antibodies directed against the cytoskeletal filaments vimentin (for fibroblasts) or cytokeratin (for epithelial cells). In a preferred confirmation protocol, cells are grown to confluency in Lab-Tek chamber slides (Nalge Nunc International). Cells are washed with PBS and fixed in methanol at 4° C. for 20 minutes. After fixation the cells are washed in PBS and blocked with 3% BSA in PBS for 15 minutes at 37° C. The block is removed and 100 μl of either a 1:40 dilution anti-vimentin clone V9 (Sigma, cat#6630) or a 1:400 dilution of anti-pan cytokeratin clone-11 (Sigma, cat#2931) is added. Slides are incubated for 1 hour at 37° C. Cells are washed with PBS and incubated for 1 hour with 100 μl of a 1:300 dilution of FITC-labeled anti-mouse IgG. Cells are washed in PBS, covered with 50% glycerol in PBS under a coverslip and observed by fluorescence microscopy. Appropriate controls for auto-fluorescence and secondary antibodies should be included.

Analysis of cell cycle stage may be performed as described in Kubota et al., *PNAS* 97: 990–995 (2000). Briefly, cell cultures at different passages are either grown to confluency and serum. After trypsinization, cells are washed with DMEM+10% FBS and re-suspended to a concentration of $5\times10^5$ cells/ml in 1 ml PBS with glucose (6.1 mM) at 4° C. Cells are fixed overnight by adding 3 ml of ice-cold ethanol. For nuclear staining, cells are then pelleted, washed with PBS and re-suspended in PBS containing 30 μg/ml propidium iodide (Sigma) and 0.3 mg/ml RNase A (Sigma). Cells are allowed to incubate for 1 hour at room temperature in the dark before filtered through a 30 um mesh. Cells may be collected on a Becton Dickenson FACs Caliber and analyzed using Cell Quest 3.1 software.

To examine the ploidy of the cultured somatic donor cells at various passages, chromosome counts may be determined at different passages of culture using standard preparation of metaphase spreads (See, e.g., Kubota et al., *PNAS* 97: 990–995 (2000)). In one embodiment, 24 hours after plating, cells are treated with hypotonic KCl (0.075M) for 15 minutes at 37° C. The cells are then fixed in acetic methanol (v:v=1:3) and drops of cell suspension are spread on clean microscopic slides. The chromosomes are stained with 5% Giemsa for 10 minutes. The numbers of well-spread chromosomes within a clear cell boundary are counted under a light microscope at 100× magnification under oil. At least 100-metaphase spreads/group should be counted.

The preferred recipient cell for the donor cell nucleus is an enucleated oocyte. A preferred enucleation techniques are described in Kubota et al., Mol. Repro. Dev. 51: 281–286 (1998) and Kubota et al., *PNAS* 97: 990–995 (2000). Briefly, enucleation may be achieved by cutting the zona pellucida with a glass needle and pushing out the polar body and the surrounding cytoplasm. Successful enucleation may be confirmed by Hoechst 3342 fluorescent staining of the presumed cytoplasts. Enucleation may also be performed by other techniques well known to those of ordinary skill in the art. For example, enucleation may involve the removal of the metaphase chromosomes from mature oocytes typically by aspirating the polar body and the adjacent cytoplasm. During the enucleation procedure oocytes may be exposed to 5 μg/ml Hoechst 33342 (plus 5 μg/ml cytochalasin B) for 5–10 minutes followed by enucleation manipulation under a fluorescent microscope.

In one preferred method, nuclear transfer is accomplished by nuclear fusion (rather than, for example, microinjection), and the cybrid is activated. In this method, cells of approximately 10–15 μm in diameter are individually picked up and transferred into the perivitelline space of enucleated oocytes. Membrane fusion is normally achieved by an electric pulse, such as an alternate current (AC) alignment pulse, followed by a direct current (DC) pulse, techniques well known to those of ordinary skill in the art.

While the electric pulse alone may also cause activation of the cybrid, it is preferred that the cells be activated further. Preferred enucleation techniques are described in Kubota et al., Mol. Repro. Dev. 51: 281–286 (1998) and Kubota et al., *PNAS* 97: 990–995 (2000). Briefly, the cybrid is activated by a DC-pulse followed by culture with cycloheximide, a potent protein synthesis inhibitor, for 5 hours. Activation may also be performed by other activation techniques well known to those of ordinary skill in the art. In one advantageous activation protocol, the manipulated oocytes are placed in Zimmerman cell fusion medium and subjected to an AC current of 0.1 kV/cm for 5–10 sec followed by a DC pulse of 1.2 kV/cm for 30 μsec using a BTX 200 unit. Fusion is determined microscopically and the fused eggs are subjected to activation by culture in KSOM medium supplemented with 10 μg/ml cytochalasin D for 1 hour and further culture in the same medium containing 10 ug/ml cycloheximide alone for 4 additional hours.

The activated cybrids or embryos are preferably cultured on a suitable medium prior to implantation in the host, e.g., uterus. It is preferred that that the activated cybrid be cultured until greater than a 2-cell development stage. In a preferred embodiment, embryos are cultured in a CR1aa medium for 48 hours at 38.5 oC in a humidified atmosphere at 5% $CO_2$, 5% $O_2$ and 90% $N_2$. Cleaved embryos may be cultured further in CR1aa medium supplemented with 5% FBS with cumulus-cell co-culture for 5 days. Blastocyts may be transferred non-surgically or surgically into the uterus of a synchronized recipient. Other medium may also be employed using techniques and media well-known to those of ordinary skill in the art. In one procedure, cloned embryos are washed three times with fresh KSOM and cultured in KSOM with 0.1% BSA for 4 days and subsequently with 1% BSA for an additional 3 days, under 5% $CO_2$, 5% $O_2$ and 90% $N_2$ at 39° C. Embryo development is examined and graded by standard procedures known in the art. Cleavage rates are recorded on day 2 and cleaved embryos are cultured further for 7 days. On day seven, blastocyst development is recorded and one or two embryos, pending availability of embryos and/or animals, is transferred non-surgically into the uterus of each synchronized foster mother.

Foster mothers preferably are examined for pregnancy by rectal palpation or ultrasonography periodically, such as on days 40, 60, 90 and 120 of gestation. Careful observations and continuous ultrasound monitoring (monthly) preferably is made throughout pregnancy to evaluate embryonic loss at various stages of gestation. Any aborted fetuses should be harvested, if possible, for DNA typing to confirm clone status as well as routine pathological examinations.

Reports made prior to the present invention (Shiels et al., *Nature* (*London*) 399: 316–317 (1999)) indicated that cloned sheep inherited the shortened telomeres of the adult nuclear donor animal (which are shortened further during the brief in vitro culture of the donor cells). These observations suggested that healthy clones might be unobtainable from aged donor animals. The present inventors have dispelled this belief with their successful cloning of four viable calves using cells from a 17 year-old bovine (Kubuta et al., *PNAS* 97: 990–995 (Feb. 1, 2000)).

It was also believed by many in the art, prior to reports by the present inventors (Kubuta et al., *PNAS* 97: 990–995 (2000)), that only female somatic nuclei could successfully be reprogrammed to drive normal embryogenesis (See, Capecchi, *PNAS* 97: 956–957 (Feb. 1, 2000)). The discovery that male somatic cells could effectively be reprogrammed to drive normal embryogenesis and to produce viable animals was unexpected in the art. It is therefore an aspect of the present invention to use male somatic cells as nuclei donors in nuclear transfer procedures.

To date, the overall cloning efficiency using somatic cells has been low, with the reported efficiency ranging form 0 to near 10%. Overall cloning efficiency by the presently disclosed invention exceeds 15%, significantly above prior art cloning efficiencies using somatic cells.

The improved method for cloning a term animal employs nuclear transfer techniques and encompasses the steps of: (a) inserting a somatic cell, or nucleus isolated from said somatic cell, deriving from a somatic cell culture having undergone 5 or more passages, into an enucleate oocyte to form a cybrid; (b) optionally activating the cybrid; (c) culturing the cybrid; (d) transferring the cybrid of step (c) into an appropriate host such that the cybrid develops into a fetus; (e) maintaining the fetus in the host until the fetus is capable of surviving and maturating into a term animal outside of said host. The cybrid, activated cybrid, fetus and animal produced during the steps of such method, and cells, nuclei, and other cellular components which may be harvested therefrom, are also asserted as embodiments of the present invention. It is particularly preferred that the term animal produced be a viable animal.

In order to more clearly describe the subject invention, the following examples are set forth along with the materials and methods used to undertake the same. The examples below are non-limiting and are merely representative of various aspects and features of the present invention.

EXAMPLE 1

Cloning of Calves from Adult Male Fibroblast Cells After Long-Term Culture

Materials and Methods
Adult Somatic Cell Collections and Culture:
A skin biopsy was obtained from the ear of a high genetic merit 17-year-old Japanese Black Beef bull. The tissue biopsy was cut into small pieces (3 mm$^2$), and the pieces as tissue explants were cultured m DMEM (GIBCO, catalog no. 12100-061) plus 10% FBS and antibiotics (GIBCO, catalog no. 15240-013) at 37.5° C. in a humidified atmosphere of 5% $CO_2$ and 95% air. After a week in culture, fibroblast cell monolayers had formed around the tissue explants. The explants were then removed, and the fibroblast cells were cultured to confluency. The cell strain was routinely maintained on dishes until passage 17 and then were stored frozen as described below. For each passage (estimated two cell doublings per passage), cells were cultured until confluent, were disaggregated by incubation in a 0.1% (wt/vol) trypsin (Difco) and EDTA (Nacalai Tesque, Kyoto) solution for 1 rain at 37° C., and were allocated to three new dishes for further passaging. Normally, each passage lasted about 6 days. For long-term storage, the cells at different passages were collected after trypsin treatment, frozen in 10% dimethyl sulfoxide (Sigma), and stored in liquid nitrogen.

Cell-Specific Markers:
Conformation of fibroblast phenotype of donor cells was conducted by immunocytochemical staining with monoclonal antibodies directed against the cytoskeletal filaments vimentin (for fibroblasts) or cytokeratin (for epithelial cells). In brief, cells, were grown to confluency in Lab-Tek chamber slides (Nalge Nunc). Cells were washed with PBS and were fixed in methanol at 4° C. for 20 min. After fixation, the cells were washed in PBS (139 mM NaCl/2.7 mM KCl/4.3 mM $Na_2HPO_4 \cdot 7H_2O$/1.48 nM $KH_2PO_4$) and were blocked with 3% BSA in PBS for 15 min at 37° C. Block was removed, and 100 µl of either a 1:40 dilution antivimentin clone V9 (Sigma, catalog no. 6630) or a 1:400 dilution of antipan cytokeratin clone-11 (Sigma, catalog no. 2931) was added. Slides were incubated for 1 h at 37° C. Cells were washed with PBS and were incubated for 1 h with 100 µl of a 1:300 dilution of FITC-labeled anti-mouse IgG. Cells were washed in PBS, were covered with 50% glycerol in PBS under a coverslip, and were observed by fluorescence microscopy. Appropriate controls for autofluorescence and secondary antibodies were included.

Cell Cycle Analyses:
Analysis of cell cycle stage was performed as described in Boquest et al., *Biol. Reprod.* 60: 1013–1019 (1999). In brief, cell cultures at different passages were either grown to confluency, were serum starved or non-starved, and were trypsinized. After trypsinization, cells were washed with DMEM plus 10% FBS and were resuspended to a concentration of 5×10$^5$ cells/ml in 1 ml of PBS with glucose (6.1 mM) and 0.5 mM EDTA at 4° C. Cells were fixed overnight by adding 3 ml of ice-cold ethanol. For nuclear staining, cells were then pelleted, were washed with PBS, and were resuspended in PBS containing 30 µg/ml propidium iodide (Sigma) and 0.3 mg/ml RNase A (Sigma). Cells were allowed to incubate for 1 h at room temperature in the dark before being filtered through a 30 µm mesh (Spectrum Laboratories). Ten-thousand cells were collected on a Becton Dickinson FACs Caliber and were analyzed by using CELL QUEST 3.1 software (Becton Dickinson).

Cell Proliferation Assay:

To examine whether the serum-starved donor cells were at quiescent stage, the ability of cells to proliferate was measured by immunofluorescence assay to detect 5-bromo-2'-deoxy-uridine (BrdUrd) incorporation into cellular DNA (Gratzner, *Science* 218: 474–475 (1982); Ellwart et al., *Cytometry* 6: 513–520 (1985)). Confluent cells at passages 5, 10, and 15 were serum starved (0.5% FBS), and cell proliferation was measured on days 1, 2, 3, 4, 5, and 6 by BrdUrd incorporation. Nonconfluent cells were also included as controls. In brief, BrdUrd labeling medium (Boehringer Mannheim, catalog no. 1296-736) was added to cell culture for 24 h at 37° C. Cells were harvested by trypsinization and were fixed by Carnoy's fixative. Fixed cell suspension was placed on clean microscopic slides overlaid with anti-BrdUrd solution and was incubated for 30 min at 37° C. After washing three times with anti-mouse Ig-fluorescein solution and an additional incubation at 37° C., the slides were mounted and examined by using a fluorescence microscope. Confluent cells at passage 5 without serum starvation were similarly measured as controls. Additionally, non-confluent cells at passages 5, 10, and 15 at day 1 of culture were also treated, and cells that had incorporated BrdUrd were counted.

Chromosome Analysis:

To examine the ploidy of the cultured somatic donor cells at various passages, chromosome counts were determined at passages 5, 10, and 15 of culture by using standard preparation of metaphase spreads (Verma et al., in *Human Chromosomes* (Pergamon, York), pp. 26–27 (1989)). In brief, 24 h after plating, cells were treated with hypotonic KCl (0.075M) for 15 min at 37° C. The cells were then fixed in acetic methanol (vol:vol=1:3), and drops of cell suspension were spread on clean microscopic slides. The chromosomes were stained with 5% Giemsa for 10 min. The numbers of well spread chromosomes within a clear cell boundary were counted under a light microscope at 1,000× magnification under oil. At least 100 metaphase spreads/group were counted.

Donor Cells and Recipient Oocyte Preparation and Nuclear Transfer:

Donor cells either were subjected to serum starvation (0.5% FBS) for 5 days after reaching confluency (passages 5, 10, and 15) or were allowed to grow for an additional 5 days in 10% serum upon confluency (cells at passage 5 only) (Wilmut et al., *Nature (London)* 385: 810–813 (1997); Campbell et al., *Nature (London)* 380: 64–66 (1996)). Immediately before nuclear transfer, donor cells were trypsinized, washed by centrifugation, and resuspended in PBS supplemented with 0.5% FBS. Recipient oocyte collection, maturation, and enucleation were as described in Kubota et al., *Mol. Reprod. Dev.* 51: 281–286 (1998) at ≈24 h after maturation culture. Successful enucleation was confirmed by Hoechst 33342 staining. Cells with an approximate diameter of 10–15 µm (Wells et al., *Biol. Reprod.* 57: 385–393 (1997)) were transferred to the perivitelline space of the recipient cytoplast using the procedure described in (Kubota et al., *Mol. Reprod. Dev.* 51: 281–286 (1998). After transfer, the cell-cytoplast complexes were induced to fuse with two pulses of direct current of 2.5 kV/cm for 10/µsec each by an Electrocell Manipulator 200 (BTX, San Diego). These electrical pulses also simultaneously induced initial oocyte activation. Fusion was then confirmed by microscopic examination. All fused embryos were further activated by culturing with cycloheximide (10 µg/ml; Sigma) in CR1aa medium (Rosenkrans et al., *Theriogenology* 35: 266 (1991)) for 5 additional hours.

In Vitro Culture of Cloned Embryos and Embryo Transfer:

The nuclear transferred embryos were cultured in CR1aa medium for 48 hours at 38.5° C. in a humidified atmosphere of 5% $CO_2$, 5% $O_2$, and 90% $N_2$. Cleavage rates were recorded, and cleaved embryos were cultured further in CR1aa medium supplemented with 5% FBS with cumulus-cell co-culture for 5 days. On day 7, blastocyst development was recorded, and one or two good quality blastocysts were transferred non-surgically into the uterus of each synchronized recipient. Recipients were examined for pregnancy by rectal palpation or ultrasonography on days 40, 60, 90, and 120 of gestation.

Genotyping of Microsatellite Markers:

To confirm the clonal status of the newborns, individual identification and parentage diagnosis were performed with 23-microsatellite markers in Inoue et al., *Animal Sci. Technol.* 68: 443–449 (1997). Total genomic DNA from the donor bull, cells of passages 5, 10, and 15, the six cloned animals, and the six foster mothers were prepared from peripheral blood leukocytes using a QIA-amp blood kit (Qiagen, Chatsworth, Calif.). PCR primers for micro-satellite markers were labeled with fluorescent dyes [6-FAM, HEX, and TET (Applied Biosystems/Perkin-Elmer)], and the DNA typing was conducted as described (Inoue et al., *Animal Sci. Technol.* 68: 443–449 (1997)). Genotypes were determined by polyacrylamide gel electrophoresis using the ABI373A DNA sequencer (Applied Biosystems/Perkin-Elmer) and were analyzed by GENSCAN 672 and GENOTYPER software (Applied Biosystems/Perkin-Elmer).

Statistical Analysis:

Embryo development experiments were repeated at least three times. Differences among treatment groups were analyzed by $\chi^2$ test.

Results:

Characterization of Donor Cells:

The cells used for cloning were systematically characterized by (i) cell type-specific marker staining, (ii) cell cycle analysis, (iii) cell proliferation assays, and (iv) chromosomal analysis.

Figure 3A:
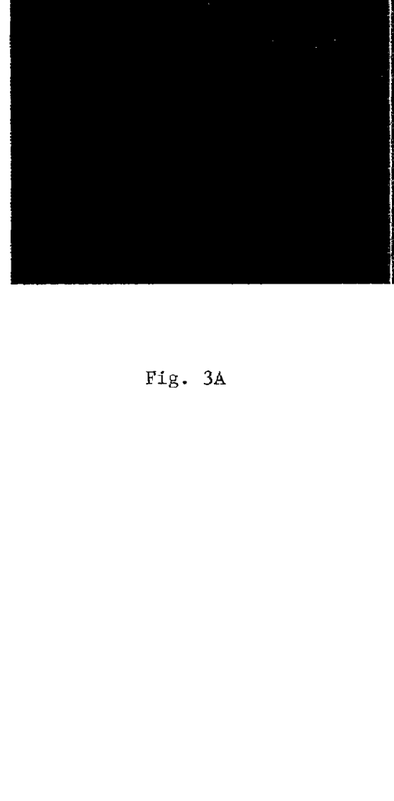
FIG. 3A is a photograph of bovine fibroblasts characterized by immunocytochemistry Vimentin-FITC.
Figure 3B:
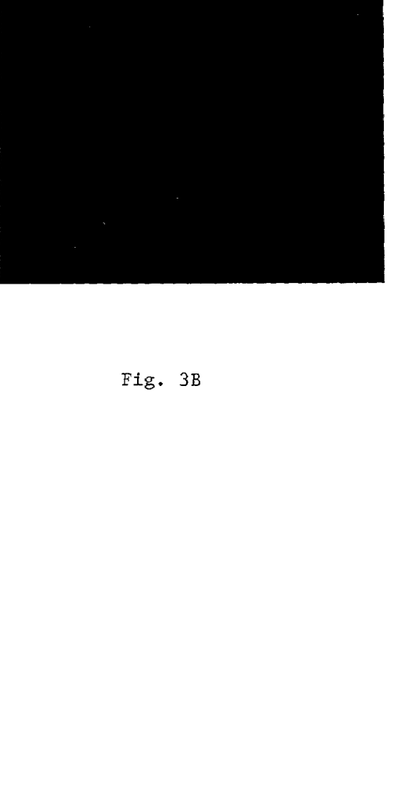
FIG. 3B is a photograph of bovine fibroblasts characterized by immunocytochemistry Cytokeratin-FITC-labeled.

To examine the specific cell type of the somatic donor cells, cultured cells were stained by cell-specific markers (cytokeratin 18 and vimentin) at passages 2, 5, 10, and 15 (FIGS. 3A and 3B). FIG. 3A demonstrates characterization of boivne fibroblasts by immunocytochemistry with Vimentin-FITC, while FIG. 3B demonstrates the characterization of such cells with Cytokeratin-FITC-label. As seen in FIG. 3, all skin cells at passages 10 and 15 were vimentin-positive, but cytokeratin-negative, demonstrating that they were fibroblast cells. A majority of cells at passages 2 and 5 were vimentin-positive and cytokeratin-negative, but a small portion of cells exhibited positive staining for cytokeratin, suggesting contamination of skin epithelial cells in the early passages. This may be partly responsible for the relatively poor development of the cloned embryos derived from cells at passage 5.

Figure 4A:
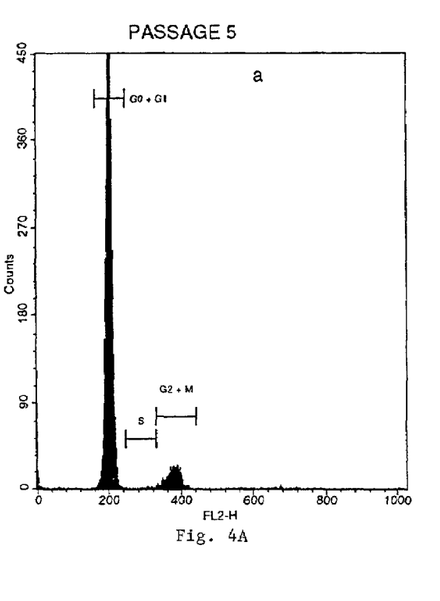
FIG. 4A is a histogram of passage 5 non-serum-starved bovine fibroblast cultures with respect to percentages of cells at each cell cycle stage.
Figure 4B:
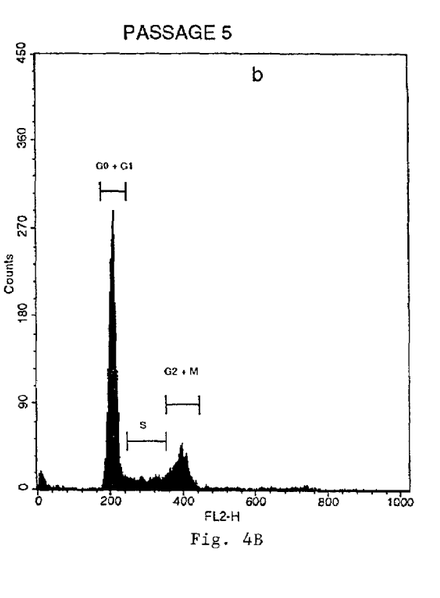
FIG. 4B is a histogram of passage 5 serum-starved bovine fibroblast cultures with respect to percentages of cells at each cell cycle stage.

FIGS. 4A and 4B show representative cell-cycle FACs histograms depicting passage 5 cells from either serum-starved vs. nonserum-starved cultures. FIG. 4A is a histogram of the passage five (5) serum-starved bovine fibroblast cultures with respect to percentages of cells at each cell cycle stage, while FIG. 4B is a histogram of the passage 5 serum-starved bovine fibroblast cultures with respect to percentages of cells at each cell cycle stage.

In the non-starved culture, 64.9±1.0% of the cells were at $G_0+G_1$ stage; upon serum starvation, the percentage of cells in $G_0+G_1$ was significantly increased to 84.5±8.1% (non-starved culture: S=7.3±0.6% and $G_2$+M=19.7±0.3%; serum-starved: S=1.1±0.8% and $G_2$+M=7.6±2.0%. At passages 10 and 15, between 82% and 90% of cultured confluent somatic donor cells were in the $G_0$+$G_1$ phase of the cell cycle, regardless of cell passage number or serum starvation treatment.

To determine the response of the cultured cells to serum starvation, cell proliferation rate was examined by BrdUrd in-corporation. Confluent cells at passages 5, 10, and 15 were subjected to serum starvation and were examined for BrdUrd incorporation daily until day six of starvation. As shown in Table 1,

TABLE 1

Cell proliferation rate (BrdUrd incorporation) of confluent cells at different passages and with or without serum starvation

| Cell passage | Serum starvation | Total cells counted (percent of cells with BrdUrd incorporation) | | | | | |
|---|---|---|---|---|---|---|---|
| | | Day 1 | Day 2 | Day 3 | Day 4 | Day 5 | Day 6 |
| 5 | No | 656 (17) | 673 (11) | 453 (4) | 457 (8) | 124 (7) | 437 (5) |
| 5 | Yes | 455 (3) | 271 (4) | 369 (4) | 389 (4) | 200 (2) | 321 (4) |
| 10 | Yes | 436 (2) | 298 (3) | 379 (0) | 262 (0) | 278 (0) | 333 (0) |
| 15 | Yes | 301 (2) | 278 (1) | 269 (0) | 161 (0) | 143 (0) | 263 (0) | serum starvation to prevent BrdUrd incorporation was more effective for cells at passages 10 and 15 than those at passage 5 for both confluent and non-confluent cultures.

Although a complete inhibition of BrdUrd incorporation was observed between 3 and 6 days of starvation in cells at passages 10 and 15, a portion (≈4%) of cells at passage 5 showed no response to serum starvation for at least 6 days (Table 1), which again suggests possible contamination of other cell types in the early passages.

Chromosomal analysis of donor cells at different passages was also made to assure a normal chromosomal complement. As is evidenced in Table 2, a majority of the cells (70–80%) showed a normal chromosomal complement (60 chromosomes including X and Y chromosomes) regardless of passage number examined.

TABLE 2

Chromosomal analysis of donor cells at different passages

| Number of cell passages | Number (%) of cells with chromosomes of: | | | Number of spreads counted |
|---|---|---|---|---|
| | <60 | 60 | >60 | |
| 5 | 8 (8) | 77 (75)* | 17 (17) | 102 |
| 10 | 7 (6) | 98 (82)* | 14 (12) | 114 |
| 15 | 19 (16) | 84 (72)* | 13 (11) | 116 |

*No significant differences (P: >0.05).

Effect of Donor Cell Passage Number on Cloning Competence:

To test the cloning competence of adult somatic cells after prolonged culture, skin fibroblast cells from a 17-year-old bull were cultured for 5, 10, and 15 passages followed by nuclear transfer assays. Table 3 sets the fusion rates, cleave rates and blastocyte formation rate for the skin fibroblast cells.

TABLE 3

In vitro developmental rates of nuclear transfer embryos derived from adult fibroblast cells at different passages

| Passage no. | Serum-starved | No. of oocytes injected | No. (%) fused | No. (%) cleaved | No. (%) of blastocysts |
|---|---|---|---|---|---|
| 5 | No | 282 | 102 (36) | 79 (78) | 28 (28)[a] |
| 5 | Yes | 288 | 114 (40) | 75 (66) | 24 (21)[a] |
| 10 | Yes | 269 | 115 (43) | 72 (63) | 43 (37)[b] |
| 15 | Yes | 264 | 109 (41) | 81 (74) | 36 (33)[b] |

As evidenced in Table 3, the fusion rates were low (36–43%, P>0.05), regardless of the donor cell treatment or passage number. At passage 5, the effect of serum starvation on nuclear transfer was tested. The rates of cleavage (66 vs. 78%) and blastocyst development (21 vs. 28%) were not different between embryos derived from serum-starved and non-starved donor cells (Table 3; P>0.05).

As evidenced in Table 4, no pregnancy was established from the nonserum-starved cells (n=10 recipients) whereas a 30% pregnancy rate (n=10 recipients; Table 4) was established from the serum-starved cells.

TABLE 4

Embryo transfer and pregnancy rates of cloned embryos from adult fibroblast cells at different passages after serum starvation

| Cell passage | No. of embryos | No. of recipients | No. (%) pregnant | No. (%) aborted | Days abortions observed |
|---|---|---|---|---|---|
| 5 | 15 | 10 | 3 (30) | 3 (100) | 61, 88, 123 |
| 10 | 22 | 14 | 9 (64) | 5 (56) | 39, 67, 69, 76, 119 |
| 15 | 17 | 12 | 3 (25) | 1 (33) | 113 |
| Total | 54 | 36 | 15 (42) | 9 (60) | |

Figure 1:
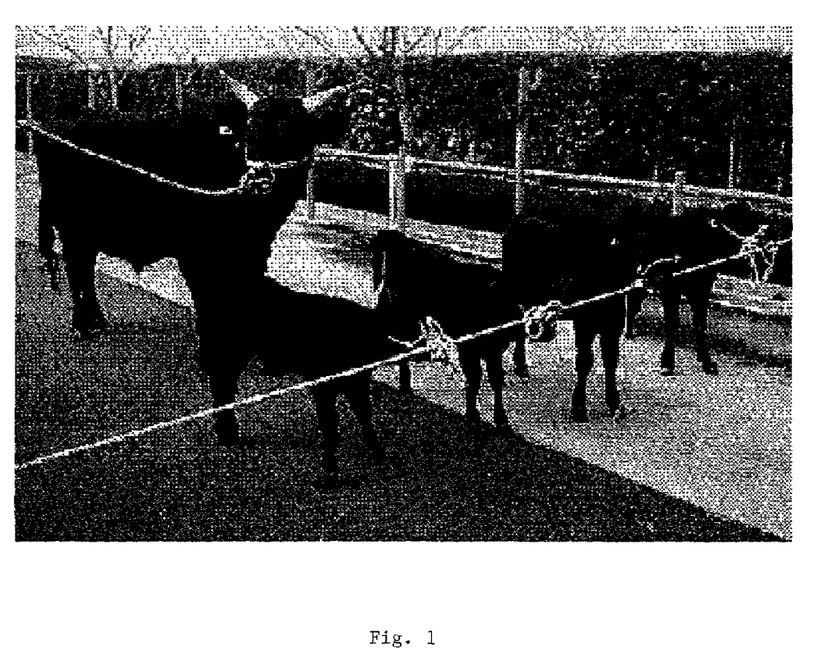
FIG. 1 is a photograph of four calves cloned using donor cells obtained from a 17-year-old bull.

Therefore, for donor cells of passages 10 and 15, serum starvation treatment was applied to all donor cells. When compared retrospectively, significantly higher rates of blastocyst development were obtained from donor cells of passages 10 and 15 than those of passage 5 (37 and 33% vs. 21%, P<0.05). After embryo transfer, nine pregnancies (n=14 recipients) from cells at passage 10 and three pregnancies (n=12 recipients) from cells at passage 15 were obtained, resulting in term development of four and two normal clone calves, respectively. The bull calves were born on Dec. 21, 23, 24, and 30, 1998 and Feb. 7 and 8, 1999, respectively (Table 3; FIG. 1). Overall, a higher pregnancy and calving rate from embryos derived from cells at passage 10 (64 and 29%) than from those at passage 15 (25 and 17%) were noted.

Analysis of the Clones:

Among the six clones born, two from passage 10 died shortly after birth. One of the deaths was caused by an infection of Akabane Virus, and the other was caused by dystocia at parturition. Postmortem autopsy revealed no gross or histopathological abnormalities in these two clones. The gestation periods for the cloned pregnancies (average, 294 days; range: 291–299 days) were 9 days longer than the average gestation period for the breed (285 days). The birth weights of the clones (average, 36 kg; range: 30.7–42.5 kg) were 20% heavier than the average birth weight for male calves of this breed (30 kg). The four surviving clones and the donor bull are shown in FIG. 1. These cloned calves as of the time of this application are 22–24 months of age. Veterinary examination of them indicate that they are healthy and normal compared with their age-matched peers derived from conventional reproduction. The measured growth curves of the cloned calves, as well as more than approximately 30 blood parameters that are indicative of the health status of a calve, found no difference between the clones and their age-matched peers.

Figure 2:
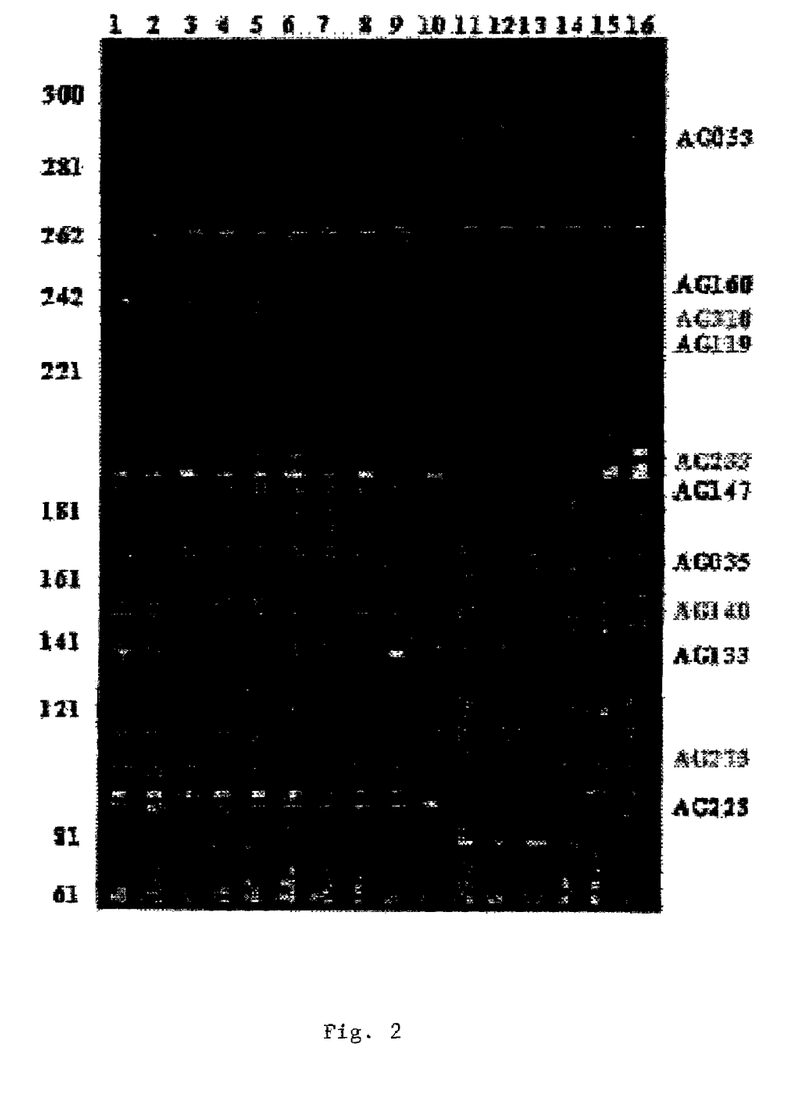
FIG. 2 is a photograph of a DNA microsatellite assay using 23 microsatellite markers for DNA obtained from a donor bull, DNA of donor somatic cells at different passages, and six clones.

To confirm the clone status of these calves, DNA typing was conducted on the six clones, the donor bull, and donor cells at passages 5, 10, and 15 by using 23 microsatellite markers (See, Inoue et al., Animal Sci. Technol. 68: 443–449 (1997)). The respective foster mothers of the clones were also included in the assays. As shown in FIG. 2, it was found that all six clones were identical to the donor bull, to the nuclear donor cells, and to each other with respect to all 23 DNA markers analyzed (lane 1: donor bull; lanes 2–4: donor cells at passages 5, 10, and 15; lanes 5–10: the six clones; lanes 11–16: the six foster mothers). Eleven sets of identical microsatellite markers were observed in lanes 1–10. Red bands, DNA molecular weight markers (in base pairs). PCR primers for microsatellite markers were labeled with fluorescent dyes: 6-FAM (blue), HEX (yellow), and TET (green). Previously, it has been shown that these 23 microsatellite markers could distinguish between 31 trillion individuals and exclude 37 million sires (See, Inoue et al., Animal Sci. Technol. 68: 443–449 (1997)).

EXAMPLE 2

Preparation of Cloned Embryos from Adult Rabbit Fibroblasts Long-Term Culture

Rabbit embryos have been successfully cloned using long term fibroblasts by the methods described herein.

Materials and Methods

Source of Oocytes and Zygotes:

Mature Dutch-belted female rabbits were superovulated (Yang et al., Mol. Reprod. Dev. 27: 110–117 (1990)) with two 0.3-mg and four 0.4-mg subcutaneous injections of FSH (FSH-P, Schering-Plough Animal Health, Kenilworth, N.J.), given 12 h apart. Twelve hours after the last FSH injection, 100 IU hCG (Sigma, St Louis, Mo.) was injected i.v. to induce ovulation. At 13.5 hours after the hCG injection, the animals were laparatomized and ovulated oocytes were flushed from the oviducts with Dulbecco-modified PBS supplemented with 3 mg/ml BSA (Fraction V, Sigma A-9418). Cumulus cells were removed by short exposure to 10 µg/ml hyaluronidase (Sigma) in D-PBS solution and subsequent pipetting with 20 a small-bore Pasteur pipette.

Enucleation of the Oocytes:

Oocytes were freed of cumulus and enucleated by a non-invasive micromanipulation procedure (Collas et. al., Biol. Reprod. 43: 877–884 (1990)). Briefly, oocytes were placed into a small drop of PBS+15% fetal bovine serum (FBS, Hyclone, Cat No. 10099-41) and 5 µg/ml cytochalasin B under oil on a depression slide. An inverted Nikon microscope equipped with Nomarski optics allowed the visualization of the nuclear chromosomes in most of the oocytes, and their removal was under visual control. However, in certain individuals the coloration and granulation of the cytoplasm made it impossible to see the chromosomes by regular light microscopy. In these cases the position of the nucleus was verified by a short (2–3 sec) exposure to UV light following staining with Hoechst 33342. The nucleus was removed with about 10% of the adjacent cytoplasm, preferably together with the first polar body. Successful enucleation was confirmed by a short UV light exposure.

Donor Cell Preparation:

Fibroblast cells were collected from an ear biopsy of an adult male rabbit. The biopsy area was shaved of fur and the surface was cleaned with 70% alcohol. A small piece of tissue was cut from the ear and washed several times in PBS with 10×antibiotic-antimycotic solution (Gibco BRL Cat. No. 15240-062), then cut into 1 mm cubes, and placed into a Petri dish to culture as explants with DMEM media plus 10% FBS. After approximately 14 days the fibroblast cells, growing out of these explants, were washed twice with $Ca^{2+}$-$Mg^{2+}$ free PBS then trypsinized. These cells were washed by centrifugation, resuspended, then used for nuclear transfer (non-passaged cells) or cultured further for up to 15 passages in DMEM media plus 10% FBS. Serum-starved cells were obtained by exposing fully confluent cell cultures to 0.5% FBS in DMEM media for 3–5 days. Cell monolayers were trypsinized, and cells were washed by centrifugation in DMEM+0.5% or 10% FBS, then incubated at 39° C. in drops until their use within 1 hour. Small (10–15 µm in diameter), smooth membrane surfaced cells were selected for nuclear transfer.

Nuclear Transfer, Embryo Culture, and Embryo Transfer:

Nuclear Transfer: The donor cells were introduced into the perivitelline space of enucleated oocytes to form cybrids. For electrofusion, the oocyte-fibroblast complexes were manually oriented in a 3.5-mm gap chamber of a BTX 200 Electro Cell Manipulator in 0.3 M mannitol solution containing 0.1 mM calcium chloride and 0.1 mM magnesium chloride, then exposed to a short, 2–3 sec AC (0.1 kV) pulse followed immediately by a 2.4 kV/cm, 60 µsec DC pulse. Cybrids were further activated by culture for 2 hours with 2.5 mM DMAP in TCM 199 containing 5.0 µg/ml cytochalasin B.

Embryo Culture: Embryos were cultured in 100-µl drops of KSOM plus 0.1% BSA for 2 days, and then replaced with KSOM plus 1% BSA for the remaining culture in a humidified atmosphere of 5% $O_2$: 5% $CO_2$: 90% $N_2$ at 39° C. Blastocyst development was recorded and blastocyst cell numbers were counted following Hoechst 33342 epifluorescein staining.

Embryo Transfer: The culture period was minimized and embryos were transferred at presumed zygote stage (after fusion evaluation) or at 2-cell stage after overnight culture. All recipient does were administered 15 µg GnRH analog (Cystorelin, Abbott Labs, Athens, Ga.) to induce ovulation for synchronization with oocyte donors. In order to increase the chance of maintaining a pregnancy with cloned embryos, some embryos were transferred into synchronous inseminated, coat-color marked recipient does (albino females mated with albino males, but received cloned embryos derived from a Dutch-belted male).

Characterization of Donor Cells:

Cell Specific Marker Staining: Immunocytochemical confirmation of fibroblast phenotype in the cultured cells used for nuclear transfer was performed by staining with monoclonal antibodies directed against the cytoskeletal filament vimentin (fibroblast-specific cell marker) or cytokeratin (epithelial cell-specific cell marker) (Franke et al., Proc. Natl. Acad. Sci. 75: 5034–5038 (1978); Franke et al., Exp. Cell Res. 123: 25–46 (1979)). Briefly, cells were grown to confluency in Lab-Tek chamber slides (Nalge Nunc International, Napemille, Ill.). Cells were washed three times with PBS and fixed in methanol at 4° C. for 20 minutes. After fixation the cells were washed three times in PBS and blocked with 3 % BSA in PBS for 15 min at 37° C. The block was removed and 100 μl of either a 1:40 dilution anti-vimentin (Vimentin clone V9, Sigma) or a 1:400 dilution of anti-cytokertin (Pan-cytokertin clone e-11, Sigma) was added. Slides were incubated for 1 h at 37° C. Cells were washed three times with PBS and incubated for 1 h with 100 μl of a 1:300 dilution of FITC labeled anti-mouse IgG. Cells were washed three times with PBS, coversliped with 50% glycerol in PBS and observed under a fluorescent microscope. Appropriate controls for auto-fluorescence and secondary antibodies were included.

Cell Cycle Determination by Flow Cytometry: Flow cytometry to determine the cell cycle stage profile was performed as known in the art (Boquest et al., Biol. Reprod. 60: 1013–1019 (1999); Prather et al., Cloning 1: 17–24 (1999)). Briefly, cells were trypsinized, resuspended in DMEM with 10% FBS at a concentration of approximately $5 \times 10^5$ cells/tube. Cells were pelleted and resuspended in 1 ml of 4° C. "saline GM" (6.1 mM glucose, 137 mM NaCl, 5.4 mM KCl, 1.5 mM $Na_2HPO_4 7H_2O$, 0.9 mM $KH_2PO_4$, 0.5 mM EDTA). Cells were fixed by slowly adding 4° C. ethanol while gently vortexing and incubated overnight at 4° C. Cells were then washed with PBS, 0.5 mM EDTA and pelleted. Cell pellets were stained for 1 h at room temperature with 30 μg/ml of propidium iodide and filtered through a 30 gm mesh (Spectrum, Los Angeles, Calif.) prior to flow cytometry. Cells were analyzed on a FACs Calibur (Becton Dickinson, San Jose, Calif.). Ten thousand cells were collected for further cell cycle analysis using the Cell Quest program (Becton Dickinson). The single parameter histogram of DNA allowed for the discrimination of cell populations existing in $Go/G_1$ (2 C DNA content), S (between 2 C and 4 C) and $G_2+M$ (4 C) phases of the cell cycle. Percentages were calculated based on the gated cells displaying fluorescence correlating to a cell cycle stage.

Results:

Out of 58 nuclear transfer fusions, 16 cybrids were seen after activation to develop into blastocysts. Non-passaged cells were found significantly less likely to develop into blastocysts.

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

What is claimed is:

1. A method of improving pregnancy rates in a female bovine, comprising:
    culturing adult bovine fibroblast donor cells in serum starved media;
    passaging the cells for at least 10 and up to 15 passages;
    nuclear transferring the donor cells into enucleated recipient bovine oocytes to form a cybrid;
    culturing the cybrid; and
    transferring the cybrid into a recipient female bovine.

2. The method of claim 1 wherein the passaging of cells is 10 passages.

3. The method of claim 2 wherein pregnancy rates are 64%.

4. The method of claim 1 wherein the passaging of cells is 15 passages.

5. A method of improving pregnancy rates in a female bovine, comprising: culturing adult bovine fibroblast donor cells in serum starved media to obtain 14, 20, or 30 doublings in cell number;
    nuclear transferring the donor cells into enucleated recipient bovine oocytes to form a cybrid;
    culturing the cybrid; and
    transferring the cybrid into a recipient female bovine.

6. The method of claim 5 wherein pregnancy rates are up to at least 64%.

7. The method of claim 5 wherein the culturing of donor cells is for 14 doublings in cell number.

8. The method of claim 5 wherein the culturing of donor cells is for 20 doublings in cell number.

9. The method of claim 5 wherein the culturing of donor cells is for 30 doublings in cell number.

10. The method of claim 1 or claim 5 wherein the fibroblast cells are obtained from a male bovine donor.

11. The method of claim 1 or 5 wherein the male bovine donor is aged.

12. The method of claim 1 or 5 wherein the aged bovine donor is 17 years old.

13. The method of claim 1 or 5 wherein the serum starved media contains up to 0.5% serum.

* * * * *